United States Patent [19]

Watanabe

[11] Patent Number: 4,756,304
[45] Date of Patent: Jul. 12, 1988

[54] ARTHROSCOPIC VIDEO CAMERA SYSTEM

[76] Inventor: Robert S. Watanabe, 11645 Wilshire Blvd., Ste. 701, Los Angeles, Calif. 90025

[21] Appl. No.: 916,944

[22] Filed: Oct. 8, 1986

[51] Int. Cl.$^4$ .............................................. A61B 1/04
[52] U.S. Cl. ........................................................ 128/6
[58] Field of Search ........................ 128/4, 6, 3, 5, 7, 9

[56] References Cited

U.S. PATENT DOCUMENTS

| Re. 31,289 | 6/1983 | Moore et al. | 128/6 |
|---|---|---|---|
| 672,317 | 4/1901 | Dow | 128/9 |
| 4,188,942 | 2/1980 | Fehlberg | 128/6 |
| 4,215,678 | 8/1980 | Heine et al. | 128/6 |
| 4,522,196 | 6/1985 | Cunningham | 128/4 |
| 4,561,429 | 12/1985 | Sato et al. | 128/6 |
| 4,590,923 | 5/1986 | Watanabe | 128/6 |

*Primary Examiner*—William H. Grieb
*Attorney, Agent, or Firm*—Keith D. Beecher

[57] ABSTRACT

An arthroscopic video camera system especially constructed to utilize a compact miniature CCD chip type of color video camera for high resolution and high light sensitivity. A disposable sterile plastic housing is provided for the camera. Prior to the arthroscopic procedure, the camera is placed in the sterile plastic housing, and is connected through a sterile electric cord to an electronic control unit. A gas sterilized adapter is attached to the front end of the camera, and the adapter is plugged into an arthroscopic mounting bracket, and a sterilized light cord extending from a remote light source is then plugged into the mounting bracket. Finally, a selected arthroscope is also plugged into the mounting bracket to be illuminated through the mounting bracket by light from the remote source, and to provide images through the mounting bracket for the video camera.

4 Claims, 3 Drawing Sheets

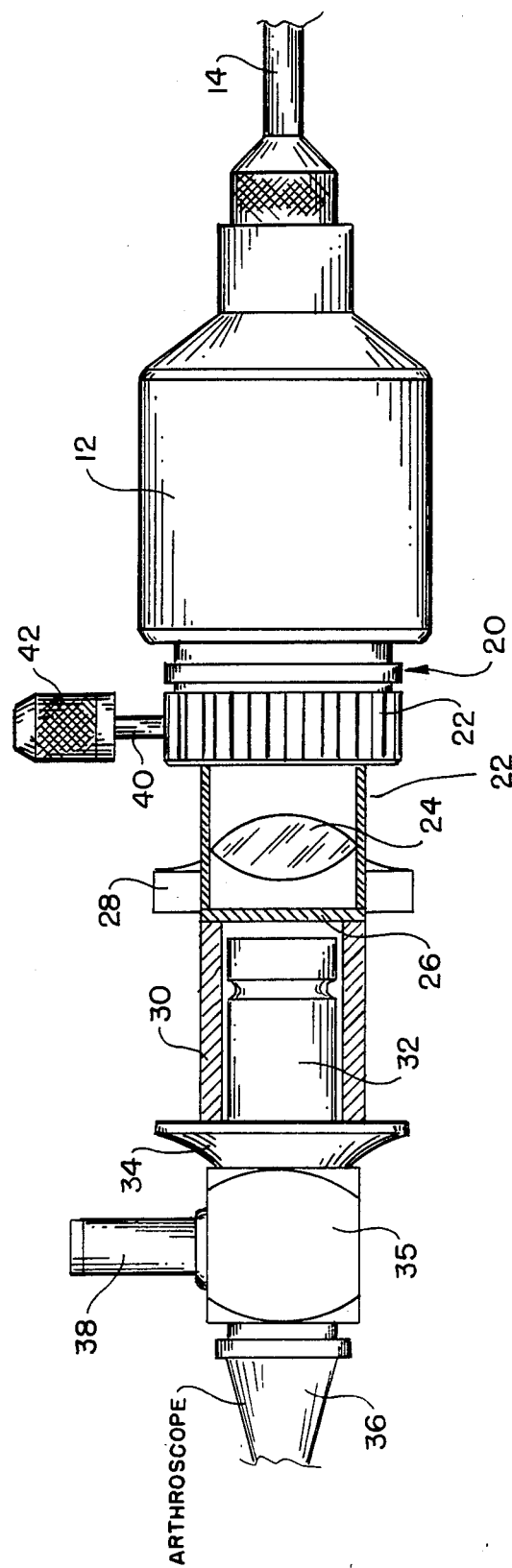

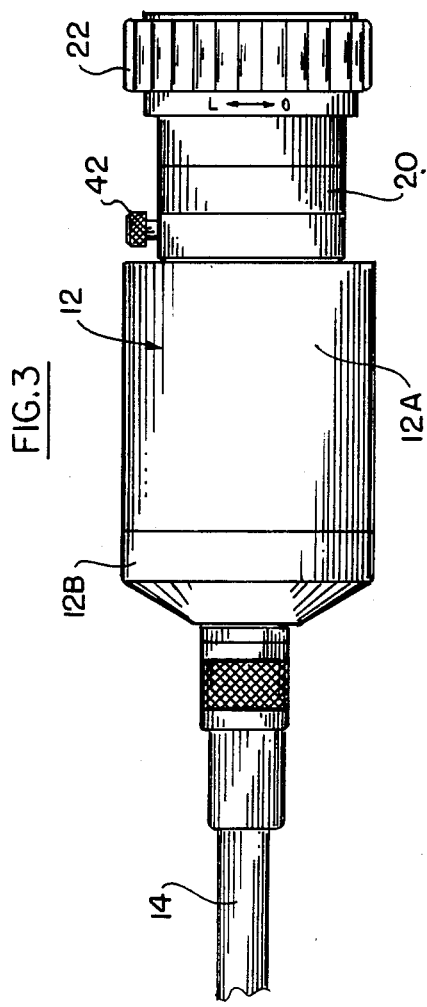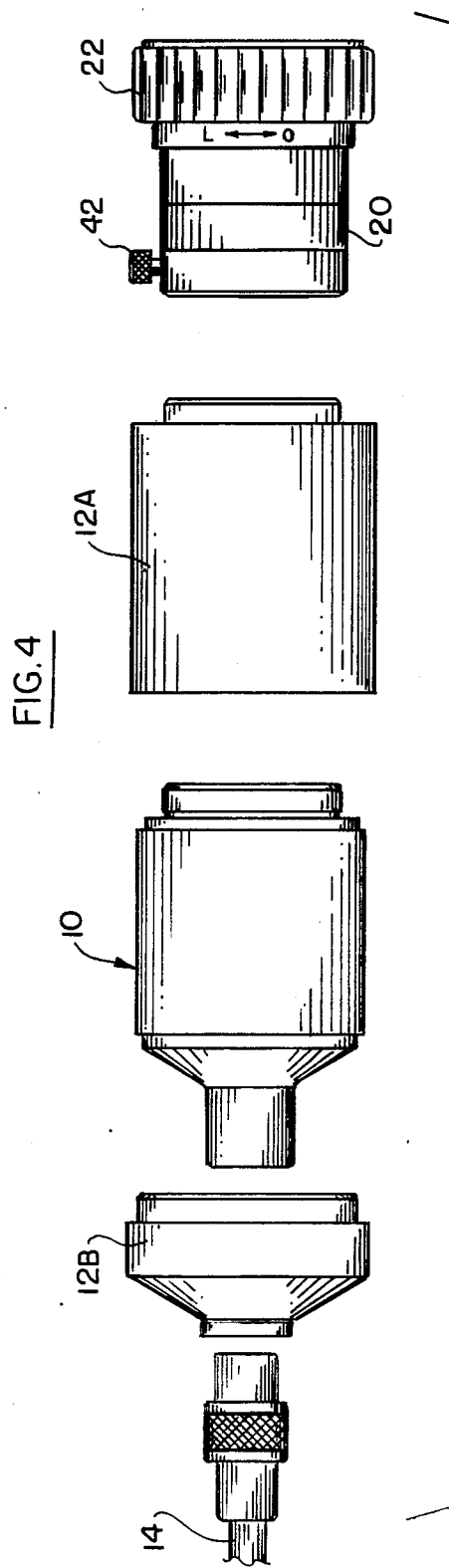

ARTHROSCOPIC VIDEO CAMERA SYSTEM

BACKGROUND OF THE INVENTION

The arthroscopic video camera system of the present invention is of the same general type described in U.S. Pat. No. 4,590,923 which issued May 27, 1986 to the present inventor.

As described in the patent, arthroscopy is a particular form of endoscopy which, in turn, is the art of examining the interior of a body cavity or hollow organ by the use of a thin tubular instrument known as an endoscope. Enscopes have been in common use since the early 20th Century. These instruments include a rigid tube containing lenses and optical glass fibers, and a lighting system by which light from an external source is conducted through the optical glass fibers to the region being examined. Endoscopes also commonly contain an irrigation system for introducing fluids, typically normal saline solutions, to the region being examined. The development of arthroscopy and instruments adapted for arthroscopic examinations, known specifically as arthroscopes, are described in an article entitled "Arthroscopy of the Knee" by Robert W. Jackson et al., Modern Orthopedic Monographs, 1976, published by Grune & Stratton, Inc. of New York.

The arthroscope, like the endoscope, is a long tube with a fiber optic light carrier which permit light to be transmitted down the tube into the body, and which further permits the doctor to view the area of the body adjacent to the distal end of the arthroscope. Arthroscopes can be particularly useful in observing the conditions within the human body. One area of the human body which arthroscopic viewing can be extremely useful is in the knee. A surgeon frequently finds it highly desirable to view the postermedial compartment of the knee in order to observe conditions in the compartment and to view the cartilage adjacent to the compartment.

The arthroscope works on the same principle as a telescope, and contains a tube with a fiber optic light carrier that lights up the joint, and glass lenses to reflect the image back to the surgeon. Some arthroscopes provide direct viewing, and others allow for 30°-70° angles.

Video systems for arthroscopy have recently been developed in which the eyepiece of the arthroscope is optically coupled to a video camera, and the arthroscopic images are displayed on the screen of a cathode-ray monitor. Such systems are marketed, for example, by the Stryker Corporation of Kalamazoo, Mich. The present invention, like the system of U.S. Pat. No. 4,590,923, is concerned with arthroscopic video systems, and the principal objective of the invention is to provide an improved arthroscopic video system and assembly.

In order to keep the video camera sterile in the arthroscopic video systems of the prior art, it was the usual practice to cover the video camera with a bag, or to soak the camera in a CIDEX solution. However, soaking the camera is not only time consuming, but does not provide a sterile unit. Soaking also served to decrease the life of the video camera.

In the system described in U.S. Pat. No. 4,590,923 referred to above, in order to overcome the problems of the prior art, the video camera is encased in a housing composed of stainless steel, the housing being first sterilized in an autoclave. In this way, the need for a plastic bag over the camera, or the need to soak the camera in a CIDEX solution, is obviated.

One feature of the system of the present invention is the provision of a sterile disposable plastic housing for the camera, in place of the stainless steel housing described in the patent. The plastic housing is received in a sterilized condition in a convenient package, and is disposed of at the end of the surgical procedure. Accordingly, any need for autoclaving of the housing is eliminated. This is because a new housing is used for each subsequent surgical procedure, with the housing being disposed of at the end of each such surgical procedure.

Accordingly, in the practice of the present invention, the arthroscopic camera has a plastic polymer case which fits directly over the camera. The case is a sterile disposable unit which eliminates the need for the camera bag or for soaking of the camera. The case is inexpensive and in conjunction with the arthroscopic adapter, it seals the camera and keeps it completely sterile.

The disposable sterile case allows for the interchange of the various arthroscopes. In other words, the surgeon is able to switch back and forth from the 30° angle to the 70° angle arthroscope with no difficulty. At the present time it is necessary to remove the plastic cover of the arthroscope by untying a string and retying when a new scope is inserted. Not only is this a very cumbersome method, but there is a significant danger of contamination due to the fact that the eyepiece of the scope is no longer sterile when it is inserted into the camera.

Another problem is that water can leak in from beneath the string area and ruin the camera. The disposable camera case costs about the same as the plastic bag that is presently in use.

Another method commonly used is to soak the camera in a Cidex solution as mentioned above. This serves to clean the camera but not provide complete sterility. This method is not permitted in most hospitals in this area because of the danger of infection. Another problem with the soaking method is that no matter how will sealed the camera, there will eventually be a leak and the solution will ruin the camera. This has been the experience of many hospitals. The soaking may also ruin the arthroscopic adapter and cause the sticking and fogging of the lens system in the adapter.

The disposable camera case of the invention is attractive and allows for ease in handling the camera. At the present time the plastic bag that is in common use causes the camera to slip around and to be difficult to handle. As mentioned, the camera case is provided in a sterile package. The entire system saves valuable operating room time and provides for a much more efficient surgical procedure.

BRIEF DESCRIPTION OF THE DRAWINGS

FIG. 2 is a side view, partly in section, showing the camera, and other components which serve optically to couple an arthroscope to the video camera;

FIG. 3 is another view of the assembly of FIG. 2; and

FIG. 4 is a detached perspective view of the assembly, showing its various components.

DETAILED DESCRIPTION OF THE ILLUSTRATED EMBODIMENT

Figure 1:
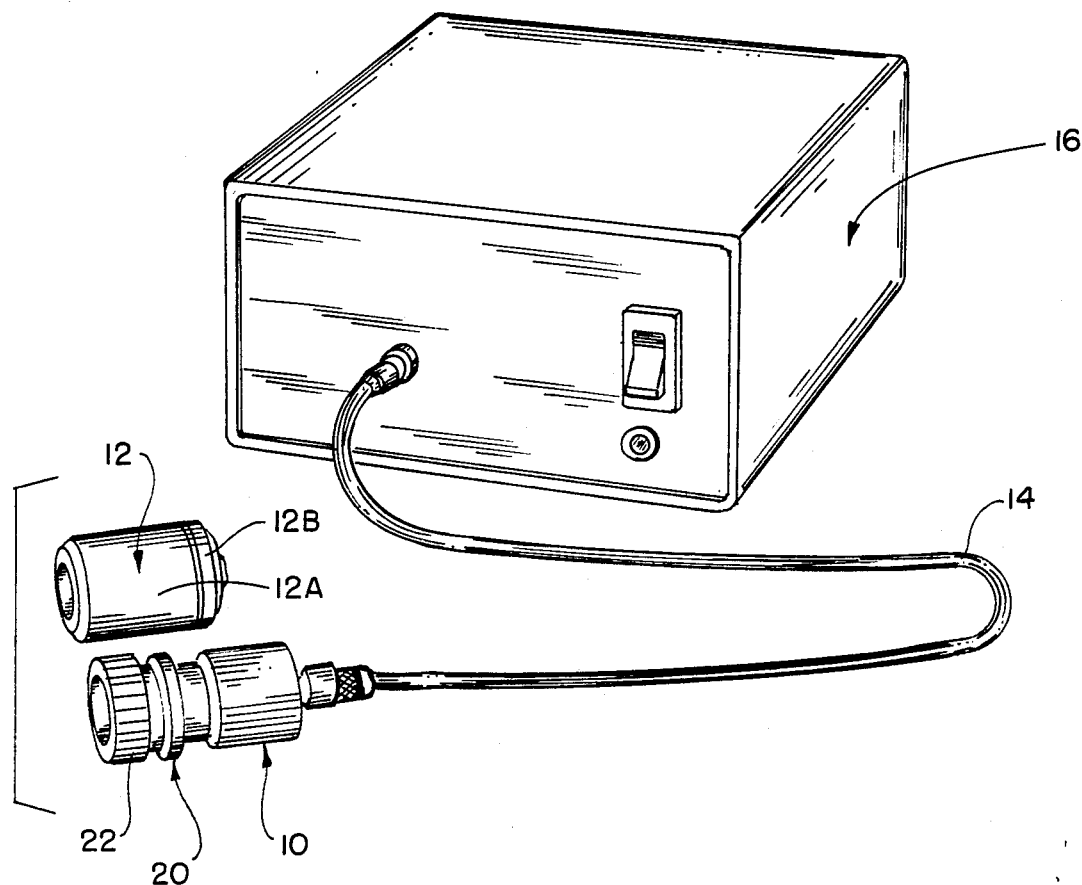
FIG. 1 is a perspective representation of a video camera for use in the system of the invention, and a control unit for the camera, together with a disposable sterile plastic housing for the camera.

A video camera designated 10 is shown in FIG. 1, and this camera preferably is a CCD chip image sensor of the type manufactured and sold, for example, by the Nippon Precision Company of Japan, and by other suppliers.

A sterile disposable polymer plastic case 12 is provided which fits over the camera. The case includes a body portion 12A and a rear cover portion 12B which fits onto the body portion. The cover portion includes a central aperture for receiving a sterile electric cord 14 which plugs into the video camera 10. The other end of cord 14 is plugged into a control unit 16 which supplies energizing power for the camera 10, and which also processes the video signals produced by the camera.

The disposable plastic case 12, when fitted over the camera 10, allows the camera to be completely sterile during use. Case 12 is preferably received in a sterile condition, in an appropriate package. After use, the case is returned to the package and disposed of. Since a new case 12 is used for each arthroscopic procedure, and since each case is received in a sterile condition, there is no need for autoclaving, or the like, as was the case with the stainless steel housing described in the patent.

The resulting camera and plastic case assembly is light and relatively inexpensive. The miniature CCD image sensor 10 provides improved resolution and light sensitivity as compared with the prior art MOS chips and video tubes. The image sensor also provides better picture stability, and decreases the tendency toward picture lag and blooming. The improved light sensitivity of the CCD image sensor 10 over the prior art video cameras allows for complete visualization of all parts of the area under observation with no blind spots. Accordingly, a smaller light source can be used, as compared with those required for the prior art cameras, resulting in a saving on space, lower heat production and lower cost.

As discussed above, the sterile plastic case 12 eliminates the need for cumbersome bags covering the camera, or the necessity of soaking the camera in a CIDEX solution. During arthroscopic procedures, the camera is placed in the sterile plastic case 12, the sterile electric cord 14 is plugged into the camera, and then a gas sterilized adapter and light cord are attached, as will be described. This provides for a completely sterile unit without the need for any bags or ties. Different types of arthroscopes may be plugged into the assembly without fear of contamination.

As shown in FIG. 1, a coupling assembly 20 is connected to the forward end of camera 10. The coupling assembly includes a rotatable ring 22, which will be described in conjunction with FIG. 2.

FIG. 2 shows the camera 10 as encased in its disposable plastic case 12, and a tubular lens housing 23 threaded into the coupling assembly 20. The lens housing 23 contains a lens 24 and a glass seal 26 at its forward end. A focus ring 28 is also provided for focusing purposes.

A further tubular housing 30 is attached to the forward end of tubular lens housing 23 in axial alignment therewith. An arthroscope adapter 32 is plugged into a bayonet type of receptacle in tubular housing 30, the adapter being provided with a water shield 34. A selected arthroscope 36 is plugged into the adapter 32. A light cord for the arthroscope is received in a connector 38.

Turning ring 22 serves to turn arthroscope 36 around the longitudinal axis of the assembly. The turning ring may be locked at any selected angular position by a radial screw 40 having a knob 42 at its outer end.

The adapter unit 32 has a sleeve (not shown) which extends into mounting bracket 35 so as to fit any of the available arthroscopes 36. As mentioned above, different arthroscopes 36 may be plugged into the mounting bracket 35, allowing the surgeon to change, for example, from 30° or 70° arthroscopes, and this may be achieved without fear of contamination.

Water shield 34 serves to prevent the leakage of water or saline solution into the interface between the arthroscope mounting bracket 35 and adapter 32. The focus ring 28 is made large enough so that the surgeon can focus readily while wearing gloves and in a wet environment. The ring 22 makes it easy to turn the arthroscope 36 about the longitudinal axis of the camera during the surgical procedure, and screw 42 provides for a positive lock in any desired angular position of the arthroscope.

The purpose of adapter 32 is to adapt the assembly to various present-day arthroscopes, so that all available arthroscopes can be used with the system. The arthroscopes can be interchanged during the procedure, as mentioned above, without fear of contamination. A bayonet-type mount is used for plugging the adapter 32 into the tubular housing 30 to provide a positive lock and prevent the adapter from coming loose during the focusing procedure.

FIG. 3 shows the camera case 12 and its associated components in an assembled condition, but with the arthroscope adaptor 32 and tubular lens housing 23 removed. FIG. 4 shows the components of FIG. 3 in a detached condition.

The invention provides, accordingly, an improved arthroscope video camera system which is relatively inexpensive, and which is constructed so as to be relatively easy to use without contamination.

It will be appreciated that while a particular embodiment of the invention has been shown and described, modifications may be made. It is intended in the claims to cover all modifications which come within the true spirit and scope of the invention.

I claim:

1. A video arthroscope system comprising: a housing; a video camera contained in said housing and enclosed therewithin; an arthroscope; a mounting bracket for detachably receiving said arthroscope, said mounting bracket being detachably mounted to one end of said housing and optically coupled to the interior of said housing for introducing optical images from the arthroscope to the video camera within the housing to be converted by the video camera into corresponding video signals; means for introducing light into the interior of said mounting bracket to enable the light to pass through said mounting bracket to said arthroscope; and a lens unit and focusing ring interposed between said mounting bracket and said one end of said housing.

2. The video arthroscope system defined in claim 1, and which includes an annular water shield interposed between said mounting bracket and said housing.

3. The video arthroscope system defined in claim 2, and which includes an adapter unit interposed between said mounting bracket and said housing to adapt the system to various types of arthroscopes; and in which said water shield is mounted on said adapter unit to prevent leakage into the interface between the adapter unit and the mounting bracket.

4. A video arthroscope system comprising: a housing; a video camera contained in said housing and enclosed therewithin; an arthroscope; a mounting bracket for detachably receiving said arthroscope, said mounting bracket being detachably mounted to one end of said housing and optically coupled to the interior of said housing for introducing optical images from the arthroscope to the video camera within said housing to be converted by the video camera into corresponding video signals; means for introducing light into the interior of said mounting bracket to enable the light to pass through said mounting bracket to said arthroscope; and a turning ring interposed between said mounting bracket and said one end of said housing for turning the arthroscope about the longitudinal axis of said camera; and a set screw extending through said housing having an adjusting knob for setting said rotation ring at any selected angular position.

* * * * *